United States Patent [19]

Ochs et al.

[11] Patent Number: 5,467,774

[45] Date of Patent: Nov. 21, 1995

[54] METHOD AND SYSTEM FOR PRECISE TIME BASED PRESENTATION OF RECORDED MEDICAL DATA

[75] Inventors: Dennis E. Ochs; David L. Burton; John F. Groh, all of McMinnville; David E. Smith, Wilsonville, all of Oreg.

[73] Assignee: Hewlett-Packard Corporation, Palo Alto, Calif.

[21] Appl. No.: 260,135

[22] Filed: Jun. 15, 1994

[51] Int. Cl.$^6$ .................................................. A61B 5/0432
[52] U.S. Cl. ............................................................ 128/711
[58] Field of Search ..................................... 128/710, 711; 360/73.08, 74.4; 346/33 M

[56] References Cited

U.S. PATENT DOCUMENTS

| | | | |
|---|---|---|---|
| 4,696,306 | 9/1987 | Shiozaki | 128/710 |
| 5,080,705 | 1/1992 | Thornton | 128/710 |
| 5,406,955 | 4/1995 | Bledsoe et al. | 128/711 |

*Primary Examiner*—William E. Kamm
*Assistant Examiner*—Scott M. Getzow

[57] ABSTRACT

The method and system for precise time based presentation of recorded medical data, such as cardiac data, encephalographic data, fetal monitor data or the like, which has been recorded on an ordinary audio cassette tape utilizing an inexpensive presentation device. An off-the-shelf tape transport deck is utilized which operates at an actual presentation speed which varies in a linear fashion in response to variations of a control signal which do not vary by greater than a selected maximum value during a given time period and in a nonlinear fashion in response to variations of a control signal which do vary by greater than the selected maximum value during a given time period. A timing track signal is utilized to determine actual presentation speed and small variations between the desired presentation speed and the actual presentation speed are coupled to a linear control system and utilized to vary the control signal at a rate which does not exceed a first rate. Large variations between the desired presentation speed and the actual presentation speed are coupled to a nonlinear control system and utilized to vary the control signal with respect to time at a constant rate, ensuring stable operation despite the occurrence of large variations in presentation speed. An integration element is utilized in conjunction with the linear control system to induce a zero steady state error between desired presentation speed and the actual presentation speed over time while the linear control system is active.

11 Claims, 5 Drawing Sheets

METHOD AND SYSTEM FOR PRECISE TIME BASED PRESENTATION OF RECORDED MEDICAL DATA

BACKGROUND OF THE INVENTION

1. Technical Field

The present invention relates in general to the field of medical instrumentation and in particular to systems for precise time based presentation of recorded medical data. Still more particularly, the present invention relates to a method and system for permitting recorded medical data to be precisely presented utilizing an off-the-shelf presentation device which varies presentation speed nonlinearly in response to large variations in a speed control signal.

2. Description of the Related Art

Modern medical science increasingly relies upon sophisticated electronic instrumentation to monitor bodily functions for diagnostic purposes and treatment regimens. Examples of these systems include electronic systems which monitor and record cardiac or encephalographic waveforms, fetal heart conditions or respiration data.

One area in which advanced electronic technology has greatly improved medical instrumentation is in the miniaturization and portability of such devices. One example of the application of this technology is the ambulatory heart recorder, such as the Hewlett-Packard Holter Recorder System. This system includes a small battery powered recorder which may be worn by the patient and which can record up to twenty-four hours of analog ECG data on a standard audio cassette tape. Typically four tracks are recorded within the audio cassette tape. Three tracks contain ECG data and a fourth track contains a timing signal. This timing signal generally comprises a thirty-two Hertz square wave timing signal.

After the patient has worn the ambulatory heart monitor for an extended period of time, the cassette tape is removed and placed within a playback system. Such playback systems generally play the tape at speeds of up to 400 times the recorded speed while digitizing and reconstructing the recorded ECG signals. These signals are then analyzed and printed so that the physician may prepare a report on the patient.

Known playback systems utilize the timing track to maintain time base accuracy throughout the playback. This is accomplished by sampling the timing signal and varying the speed of a highly accurate playback system to obtain the desired sample rate. The American Association for the Advancement of Medical Instrumentation (AAMI) requires that this time base be accurate to plus or minus fifteen seconds over a twenty-four hour period. As a result, the playback systems utilized in such systems are typically highly accurate and quite expensive such that the speed of playback may be linearly and accurately controlled.

While the system described above is highly reliable and accurate for recording and presenting time based medical data, it should be apparent that it would be advantageous to provide a system which permits the playback of time based medical data in a highly accurate manner utilizing inexpensive off-the-shelf tape transport devices.

SUMMARY OF THE INVENTION

In one aspect the present invention relates to an improved medical instrumentation system.

In another aspect of the present invention, the presentation of time based recorded medical data may be precisely controlled.

In yet another aspect of the present invention, a method and system are provided for permitting recorded medical data to be precisely presented utilizing an off-the-shelf presentation device which varies in speed nonlinearly in response to large variations in a speed control signal.

The method and system of the present invention may be utilized for precise time based presentation of recorded medical data, such as cardiac data, encephalographic data, fetal monitor data or the like, which has been recorded on an ordinary audio cassette tape utilizing an inexpensive presentation device. An off-the-shelf tape transport deck is utilized which operates at an actual presentation speed which varies in a linear fashion in response to variations of a control signal which do not vary by greater than a selected maximum value during a given time period and in a nonlinear fashion in response to variations of a control signal which do vary by greater than the selected maximum value during a given time period. A timing track signal is utilized to determine actual presentation speed and small variations between the desired presentation speed and the actual presentation speed are coupled to a linear control system and utilized to vary the control signal at a rate which does not exceed a first rate. Large variations between the desired presentation speed and the actual presentation speed are coupled to a nonlinear control system and utilized to vary the control signal with respect to time at a constant rate, ensuring stable operation despite the occurrence of large variations in presentation speed. An integration element is utilized in conjunction with the linear control system to induce a zero steady state error between desired presentation speed and the actual presentation speed over time while the linear control system is active.

The above as well as additional aspects, features, and advantages of the present invention will become apparent in the following detailed written description.

BRIEF DESCRIPTION OF THE DRAWINGS

The novel features believed characteristic of the invention are set forth in the appended claims. The invention itself, however, as well as a preferred mode of use, further objectives and advantages thereof, will best be understood by reference to the following detailed description of an illustrative embodiment when read in conjunction with the accompanying drawings, wherein:

DETAILED DESCRIPTION OF PREFERRED EMBODIMENT

Figure 1:
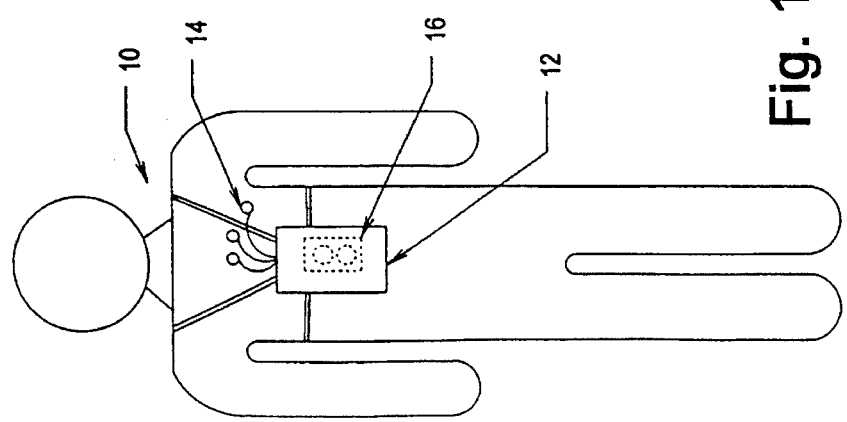
FIG. 1 is a pictorial representation of a patient wearing an ambulatory heart monitor recorder.

With reference now to the figures and in particular with reference to FIG. 1, there is depicted a pictorial representation of a patient wearing an ambulatory heart monitor and recorder. As illustrated, a patient 10 is depicted wearing an ambulatory heart monitor and recorder 12, such as the Hewlett-Packard Holter Recorder System. As depicted within FIG. 1, this system utilizes a standard audio cassette tape 16 to record analog electrocardiographic signals which are detected within patient 10 utilizing multiple electrodes 14. As described above, systems such as the one depicted within FIG. 1 may record up to forty-eight hours of analog electrocardiographic data on a standard audio cassette tape utilizing three tracks of that tape for the electrocardiographic data. A fourth track typically contains a timing signal which generally comprises a thirty-two Hertz square wave.

Figure 2:
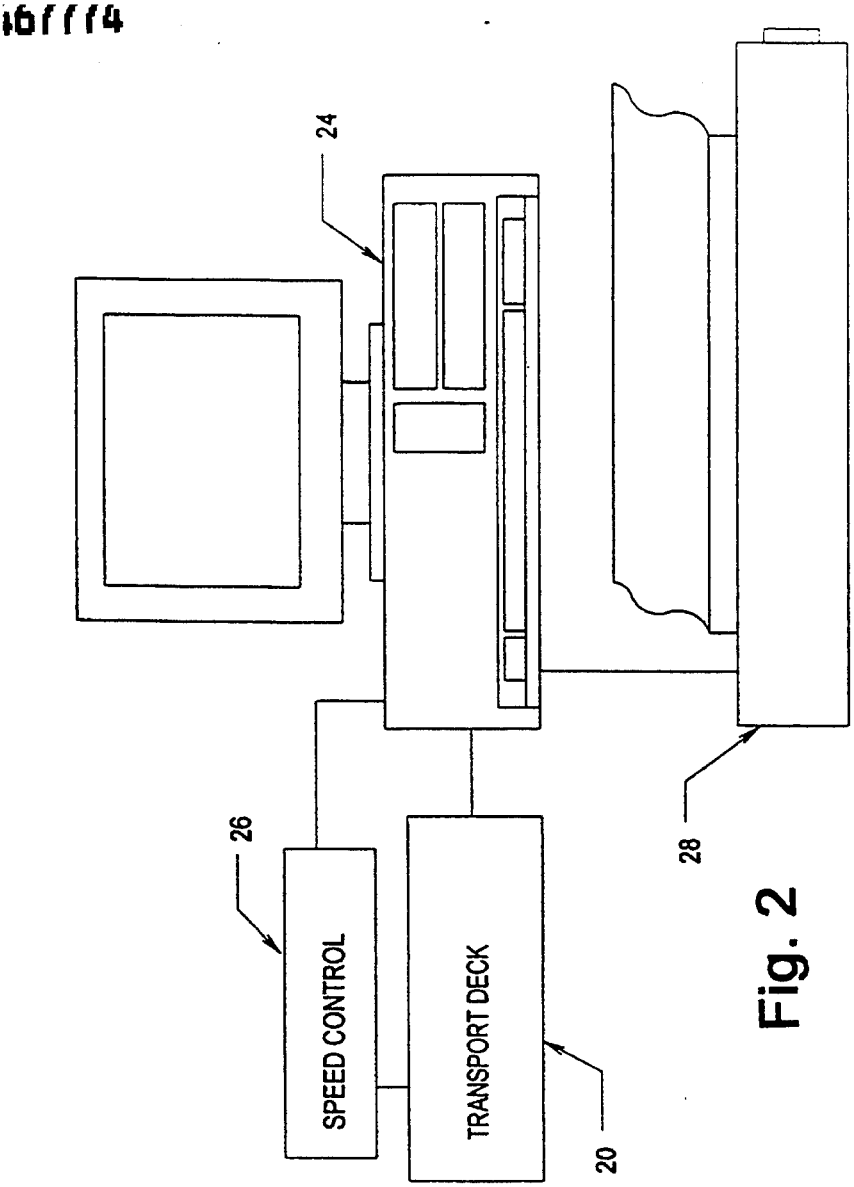
FIG. 2 and is a high level block diagram of a playback system which may be utilized in conjunction with an ambulatory heart monitor system of the type illustrated within FIG. 1.

Referring now to FIG. 2, there is depicted a high level block diagram of a playback system which may be utilized in conjunction with the ambulatory heart monitor system of FIG. 1. As illustrated, a transport deck 20 is depicted. In accordance with the method and system of the present invention, a standard off-the-shelf tape transport deck, such as the Texel MM200 transport deck, may be utilized to precisely present the recorded medical data in a manner which satisfies time base accuracy requirements utilizing the novel two-state control system of the present invention. As illustrated, transport deck 20 is coupled to a computer 24 which, in one embodiment of the present invention, may be utilized to control the processing of recorded data. A speed control circuit 26 is also depicted and may be utilized, in accordance with the method and system of the present invention, to control the presentation speed of transport deck 20 in a manner which will be explained in greater detail herein. Speed control 26 may be partially implemented utilizing software routines and an associated microprocessor and may, in one depicted embodiment of the present invention, utilize specific hardware circuitry as will be described in greater detail herein.

The electrocardiographic data recorded on audio cassette tape 16 may also be utilized to create a printed copy of various segments of that data utilizing a printer 28, which is coupled to computer 24, in a manner well known to those having ordinary skill in the art.

Figure 3:
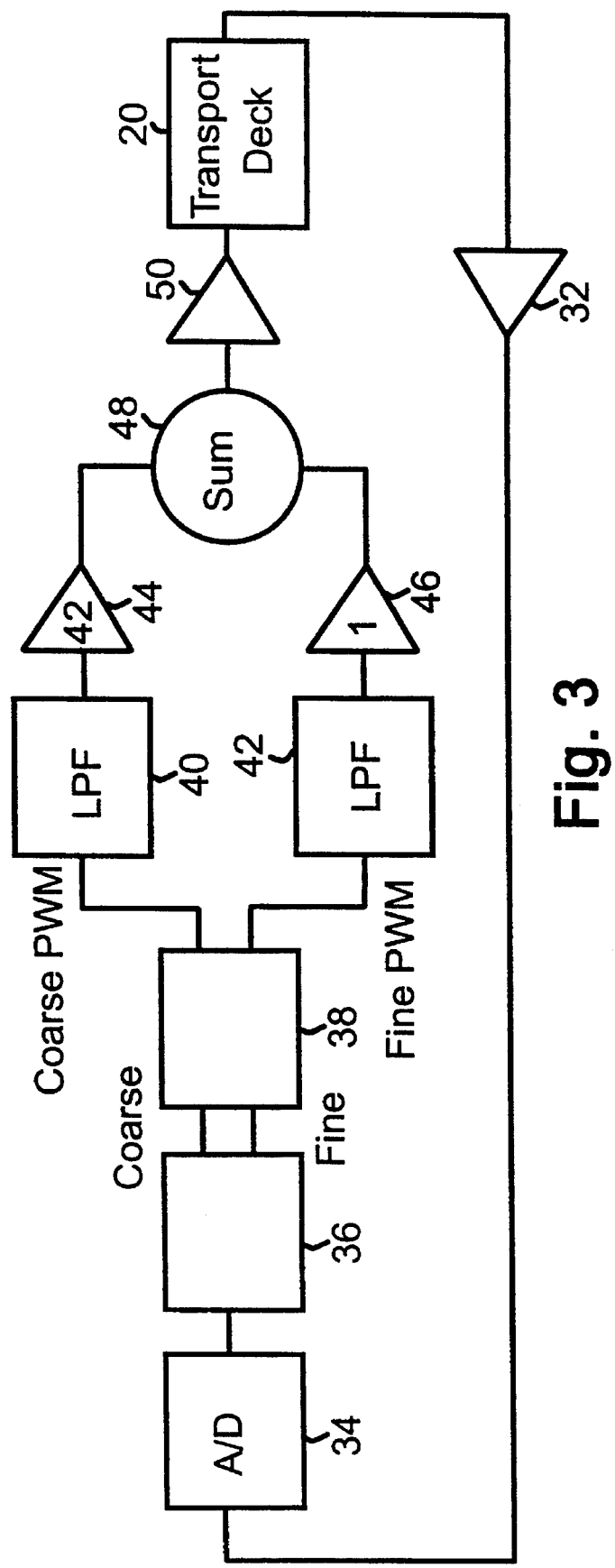
FIG. 3 is a high level hardware block diagram of a two-state speed control system utilized in accordance with the method and system of the present invention.

With reference now to FIG. 3, there is depicted a high level hardware block diagram of a two-state speed control system which may be utilized in accordance with the method and system of the present invention. As illustrated, transport deck 20 is the device being controlled. The Texel MM200 transport deck is capable of playing an analog cassette tape at speeds which range from 100 to 400 millimeters per second. Ambulatory heart recorders of the type depicted within FIG. 1 typically record electrocardiographic data at a rate of approximately one millimeter per second. In the depicted embodiment of the present invention transport deck 20 is preferably utilized to playback the recorded analog electrocardiographic data at speeds of up to 400 times its original recorded speed while digitizing and reconstructing those signals. This data may then be analyzed utilizing computer 24 (see FIG. 2) and utilized by the physician to prepare a report.

As those skilled in the art will appreciate a tape transport deck such as the Texel MM200 controls playback speed by means of a speed control voltage level which is coupled to an analog speed control input. The actual presentation speed may be measured by observing the frequency of the timing track discussed above, as that track is detected by the magnetic playback heads within the transport deck. The Texel MM200 utilized to implement transport deck 20 includes a four track playback head which may be utilized to simultaneously sense the four tracks of data on the standard audio cassette tape. In the depicted embodiment of FIG. 3, only the timing signal output is depicted.

Transport deck 20, when implemented utilizing a Texel MM200 transport deck, has a steady-state output speed which is a linear function of its steady state input voltage, as set forth in equation one.

$$S_{outss} = K_1 * V_{inss} + K_2 \qquad \text{Equation 1}$$

Where $K_1$ and $K_2$ are constants which are empirically derived. Thus, for applications of the present invention, if utilizing alternate tape transport devices, these constants must be empirically derived for those devices.

However, when utilizing an off-the-shelf tape transport deck such as the Texel MM200, a large increase in the voltage applied to the analog speed control input, such as a step change, results in a nonlinear variation in the presentation speed of the device. That is, the presentation speed responds with a constant acceleration until such time as the new desired presentation speed has been achieved. During such transitions, the dynamic output speed response of the Texel MM200 transport deck is given as follows:

$$S_{out}(t_2) = S_{out}(t_1) + A(t_2 - t_1) \qquad \text{Equation 2}$$

Where A is the acceleration constant for the playback deck being utilized. This value may be positive or negative, depending upon the sign of the direction of the input change. As above, this equation may be empirically derived for a particular tape transport deck being utilized.

As those skilled in the art will appreciate upon reference to the foregoing when the voltage level at the analog speed control input of the transport deck varies faster than the presentation speed can respond, the speed of transport deck 20 is described by Equation 2. In situations in which the voltage applied to the analog speed control input varies at a rate which is slower than the acceleration constant A, Equation 1 describes the output speed of transport deck 20. This non-linear behavior in response to large variations in voltage level applied to the analog speed control input of the deck requires a special two-state control system which is implemented in accordance with the method and system of the present invention in order to obtain the required accuracy for these purposes.

Still referring to FIG. 3, the timing track signal of transport deck 20 is applied to a preamplifier 32 and then coupled to analog-to-digital converter 34. In the depicted embodiment of the present invention, analog-to-digital converter 34 is preferably a one hundred kilohertz sixteen bit analog-to-digital converter. The output of analog-to-digital converter 34 is then coupled to digital signal processor 36. Digital signal processor 36 is preferably implemented utilizing a Model 56002 digital signal processor manufactured by Motorola Incorporated Communications. Digital signal processor 36 preferably receives the sixteen bit samples from analog-to-digital converter 34 through its Synchronous Serial Interface (SSI) port at the rate of 100,000 kilohertz samples per second. Each input sample produces an interrupt within digital signal processor 36. The Synchronous Serial Interface (SSI) Interrupt Service Routine (ISR)

detects and counts each cycle of the timing track signal. Each time a new timing track cycle is detected, a variable called "COUNT" is incremented, which is utilized to measure the frequency of the timing track signal.

Another interrupt from the Serial Communication Interface (SCI) port within digital signal processor 36 is preferably utilized to implement the two-state control system of the present invention. This port is programmed to be a general purpose timer which produces an interrupt at a programmable rate. The two-state control system of the present invention thus operates in a linear or non-linear mode. In the linear mode, the Serial Communication Interface (SCI) port is programmed to produce an interrupt at 100 hertz, and in a non-linear mode this port is programmed to produce an interrupt at twenty hertz. Thus, with each Serial Communication Interface (SCI) interrupt, digital signal processor 36 computes and outputs two digital signals which are referred to herein as "FINE" and "COARSE," which are coupled to microprocessor 38. The "FINE" signal is utilized by the linear control system and the "COARSE" signal is utilized by the nonlinear control system. In the depicted embodiment of the present invention, these signals cannot change simultaneously.

Microprocessor 38 preferably communicates with digital signal processor 36 through the digital signal processor Host Interface port. Microprocessor 38 receives an interrupt each time a new value of "FINE" or "COARSE" is presented to it. On each Interrupt Service Routine (ISR), microprocessor 38 reads the value of "FINE" and "COARSE" from the digital signal processor 36 and then immediately copies each of these values to separate pulse width modulator (PWM) outputs. These pulse width modulator outputs are sixteen kilohertz digital signals having a duty cycle which may vary between 0 and 100%. A value of 0 written to a pulse width modulator control register produces a 0% duty cycle and a value of 200 written to a pulse width modulator control register produces a 100% duty cycle, in the depicted embodiment of the present invention.

Next, the "COARSE" and "FINE" pulse width modulator signals are coupled through low pass filters 40 and 42 which serve to convert the digital pulse width modulated signals into analog signals. These analog signals are then summed together in a manner such that the value of "COARSE" is give forty-two times more gain than the value of the "FINE" signal, as illustrated utilizing amplifiers 44 and 46. The output of amplifiers 44 and 46 are then summed utilizing summer 48 and coupled, via amplifier 50 to the analog speed control input of transport deck 20.

As discussed above, in order to meet published specifications with regard to the accuracy of the time base utilized for presentation of this recorded data, the steady-state error of the control system must be exactly zero. This means that the control loop must include an integrater which keeps a running sum of the error over the duration of the tape. The control system should then control the speed in order to make the integral of the error a finite constant. This approach will guarantee a steady-state error of zero; however, an integrater circuit introduces a −90° phase shift to the loop gain transfer function.

As set forth above, in Equation 2, the Texel MM200 tape transport deck is inherently a nonlinear system. Thus, for any fixed amplitude input signal this deck acts like a linear system with a dominant low pass pole. This dominant pole adds another −90° to the loop gain transfer function. Unfortunately, the location of this "pole" is inversely proportional to the signal amplitude. That is, the 37 pole" may be moved arbitrarily close to zero hertz by applying a sufficiently high amplitude input signal. For stability in a linear control system, the loop gain must be less than 1 at the frequency in which the loop phase becomes −180°. Therefore, any integrating linear control system for a system such as the one described herein, may become unstable with a sufficiently-large input disturbance.

In order to solve this problem, a two-state control system is implemented utilizing digital signal processor 36 in a manner which is described herein. This two-state control system is always either in a linear mode or a nonlinear mode. In a linear mode, digital signal processor 36 implements an integrating linear control loop which has a zero steady state error. In a nonlinear mode, digital signal processor 36 implements a nonlinear, nonintegrating control system which is inherently stable. The nonlinear control system has a small, but non-zero steady state error. Thus, while the control system will operate in a linear mode when input disturbance amplitudes (whether positive or negative) are less than a preselected threshold value in a given period of time, that threshold must be chosen such that the linear control system will always be stable while it is in operation. The control system will then operate in a nonlinear mode whenever disturbances (positive or negative) are applied to the analog speed control input of transport deck 20 which are greater than this preselected threshold in a given period of time. The design of the nonlinear control system must guarantee stability for any disturbance.

Thus, the two-state control system of the present invention will always attempt to operate in a linear mode whenever possible. Ideally, the two-state control system utilizes the nonlinear control system to set the presentation speed of transport deck 20 very close to the desired presentation speed. Thereafter, the control system will switch to the linear mode and remain there for the entire tape scan. This allows the control system to meet the specifications noted above for time based accuracy. The nonlinear control system also serves as a safety net in the event of a defective or low quality recorder which introduces large speed changes which would otherwise cause the linear control system to become unstable.

Figure 4:
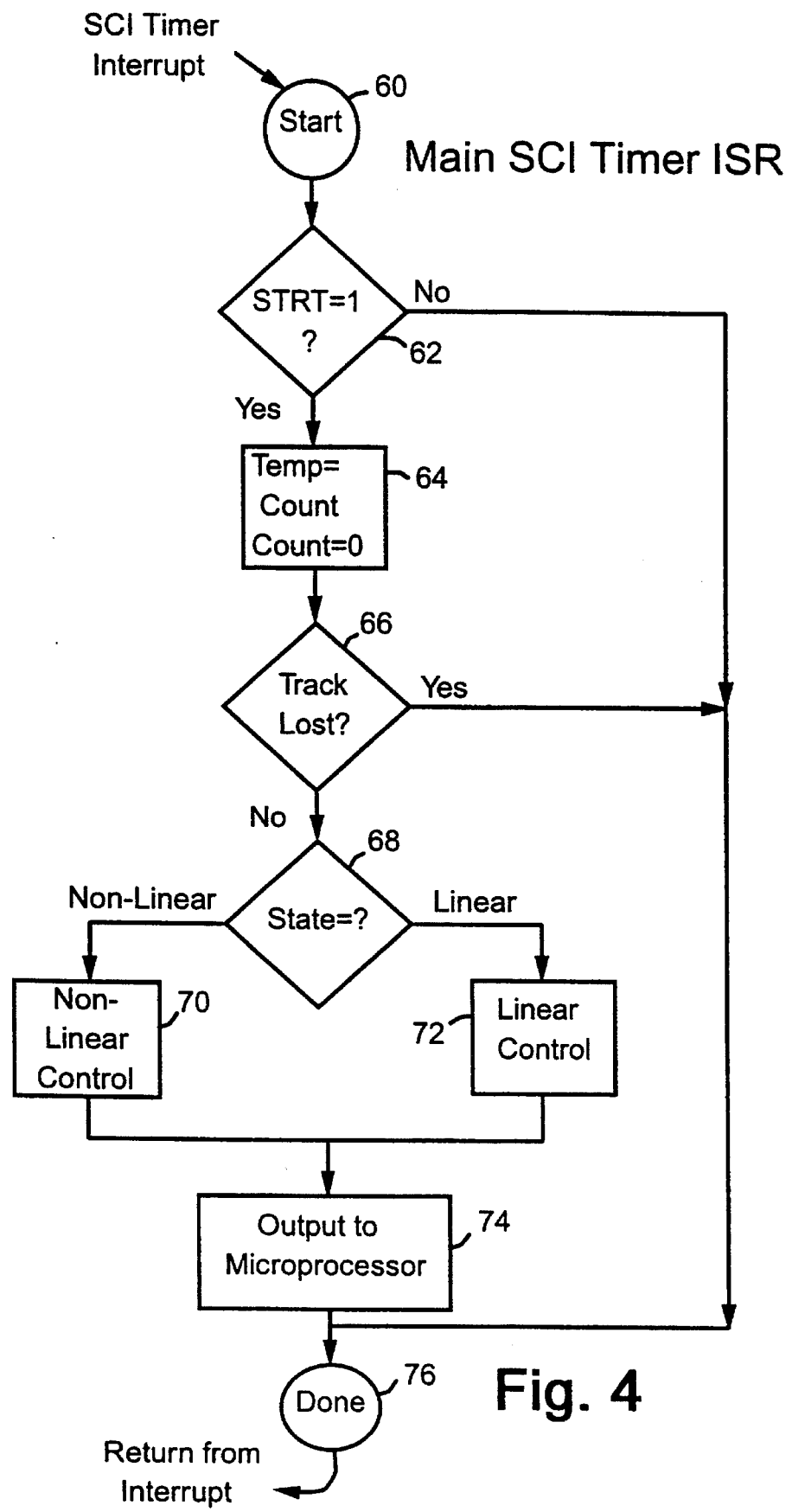
FIG. 4 is a high level flow diagram of a two-state speed control system utilized in accordance with the method and system of the present invention.

Referring now to FIG. 4, there is depicted a high level flow diagram of a two-state control system which may be utilized in accordance with the method and system of the present invention. As described above, the digital controls system of the present invention is implemented utilizing a digital signal processor and an interrupt from the Serial Communication Interface (SCI) port of that digital signal processor. In the linear mode of operation, this interrupt service routine is called at a rate of 100 Hertz and in the nonlinear mode it is called at 20 Hertz. The process of FIG. 4 begins at block 60 and thereafter passes to block 62 which illustrates a determination of whether or not a bit "STRT" is set to indicate that a valid timing track signal has been observed. This bit is originally clear and is set by the (SSI) Interrupt Service Routine (ISR) after it has detected a minimum number of timing track pulses as described above. If this bit is set, the SCI Interrupt Service Routine (ISR) then copies the value of the variable "COUNT" to another variable called "TEMP" and clears the variable "COUNT", as illustrated in block 64.

The variable "TEMP" now contains the number of timing track pulses detected by the SSI Interrupt Service Routine (ISR) since the previous SCI interrupt was detected and its value is a measurement of the timing track frequency. Based upon the value of the variable "TEMP" the SCI Interrupt Service Routine (ISR) then determines whether the timing track is still valid, as depicted at block 66. If the timing track is still valid, the SCI Interrupt Service Routine (ISR) then calls either the nonlinear or linear control system as illustrated by the determination at block 68. The resulting "COARSE" and "FINE" values generated during nonlinear control or linear control, as illustrated at blocks 70 and 72 are then coupled to the transport deck, as illustrated at block 74. The process then returns, as depicted at block 76.

In the depicted embodiment of the present invention, the two-state control system always begins operation in a nonlinear mode which then switches to the linear mode after setting the presentation speed of transport deck 20 close to the desire presentation speed. Referring again to blocks 62 and 66, in the event the "STRT" bit is not set or the track has been lost, the process passes directly to block 76 and returns without changing the value of "COARSE" or "FINE."

Figure 5:
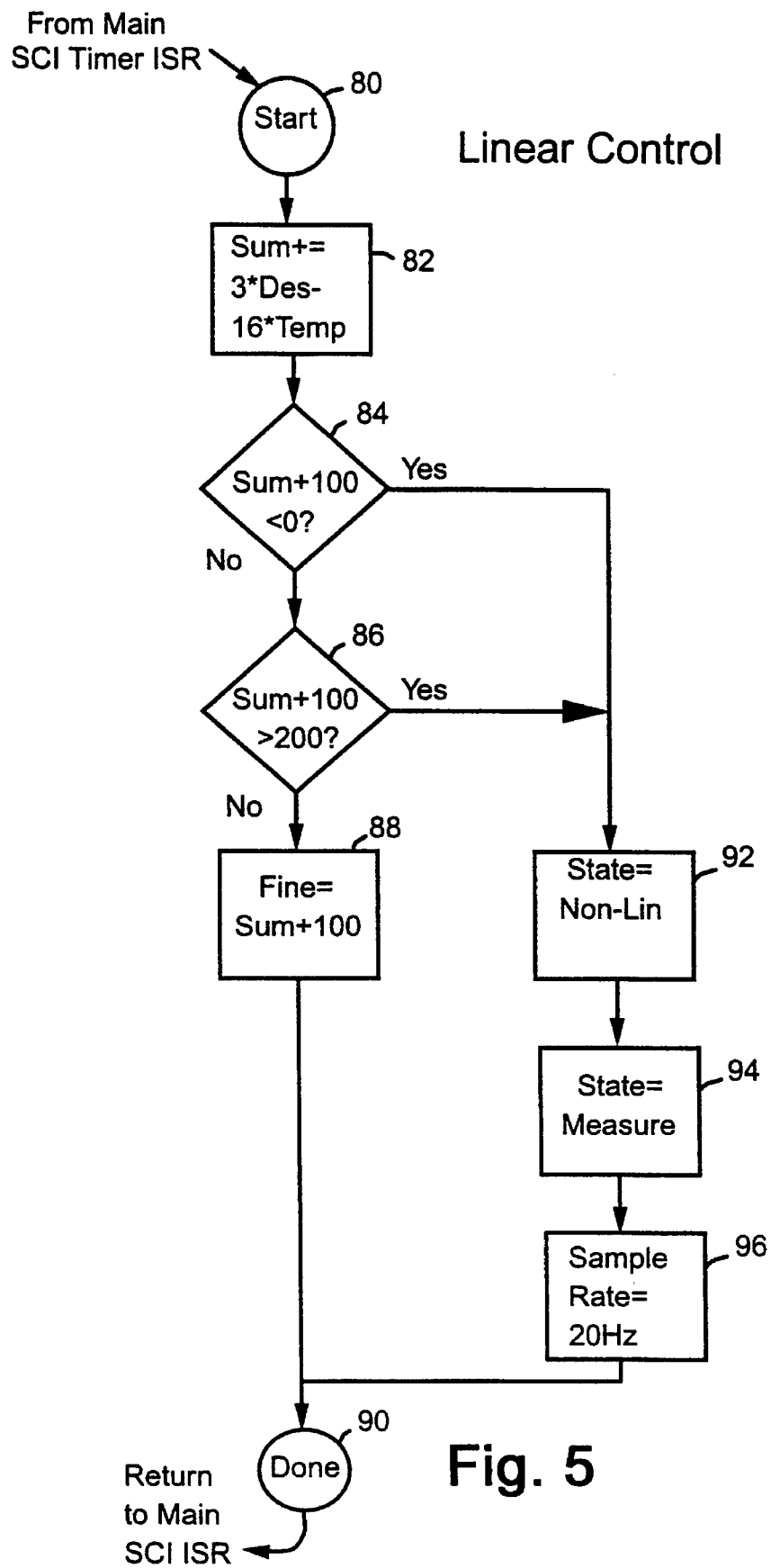
FIG. 5 is a high level flow diagram of a linear control circuit constructed in accordance with the method and system of the present invention.

With reference now to FIG. 5, there is depicted a high level flow diagram of a linear control circuit which is constructed in accordance with the method and system of the present invention. As illustrated, the linear control function depicted within FIG. 5 is called from the two-state control system flow diagram which is depicted within FIG. 4. This task is preferably executed 100 time per second, while the control system operates in a linear mode. This process begins, as illustrated at block 80 and thereafter passes to block 82. As described above, the method and system of the present invention always begins operation in the nonlinear mode which is utilized to adjust the actual presentation speed to a value which is close to the desired presentation speed. The variable "SUM" contains the integral of the error between actual presentation speed and desired presentation speed and, before the linear control system may become active, "SUM" is set to zero and the value of "COARSE" is set such that the calculated value of "FINE" should be approximately 100. Recall that the calculated value of "FINE" in the depicted embodiment of the present invention may vary between 0 and 200. Block 82 illustrates an integration of the error by incrementing "SUM" by a multiple of the desired target speed (DES) and the variable "TEMP" which represents the measured actual speed.

Next, the process passes to block 84. Block 84 illustrates a determination of whether or not "SUM" plus 100 is less than 0. If so, the process passes to block 92 which changes the state of the control system to the nonlinear state. The process then passes to block 94 which illustrates the initialization of the substate of the non-linear control system, to the "Measurement" substate. Thereafter, as illustrated at block 96, the sample rate is decreased to 20 hertz while operating in the nonlinear mode and the process then passes to block 90 and returns.

Referring again to block 84, in the event "SUM" plus 100 is not less than 0, block 86 illustrates a determination of whether or not "SUM" plus 100 is greater than 200. Again, if this condition exists the process passes to block 92 in the manner described above to change the state to the control system from linear to nonlinear.

Referring again to block 86, in the event that "SUM" plus 100 is not greater than 200, the process passes to block 88 which illustrates the setting of the value of "FINE" to compensate for this error and the process then returns, as depicted at block 90.

Figure 6:
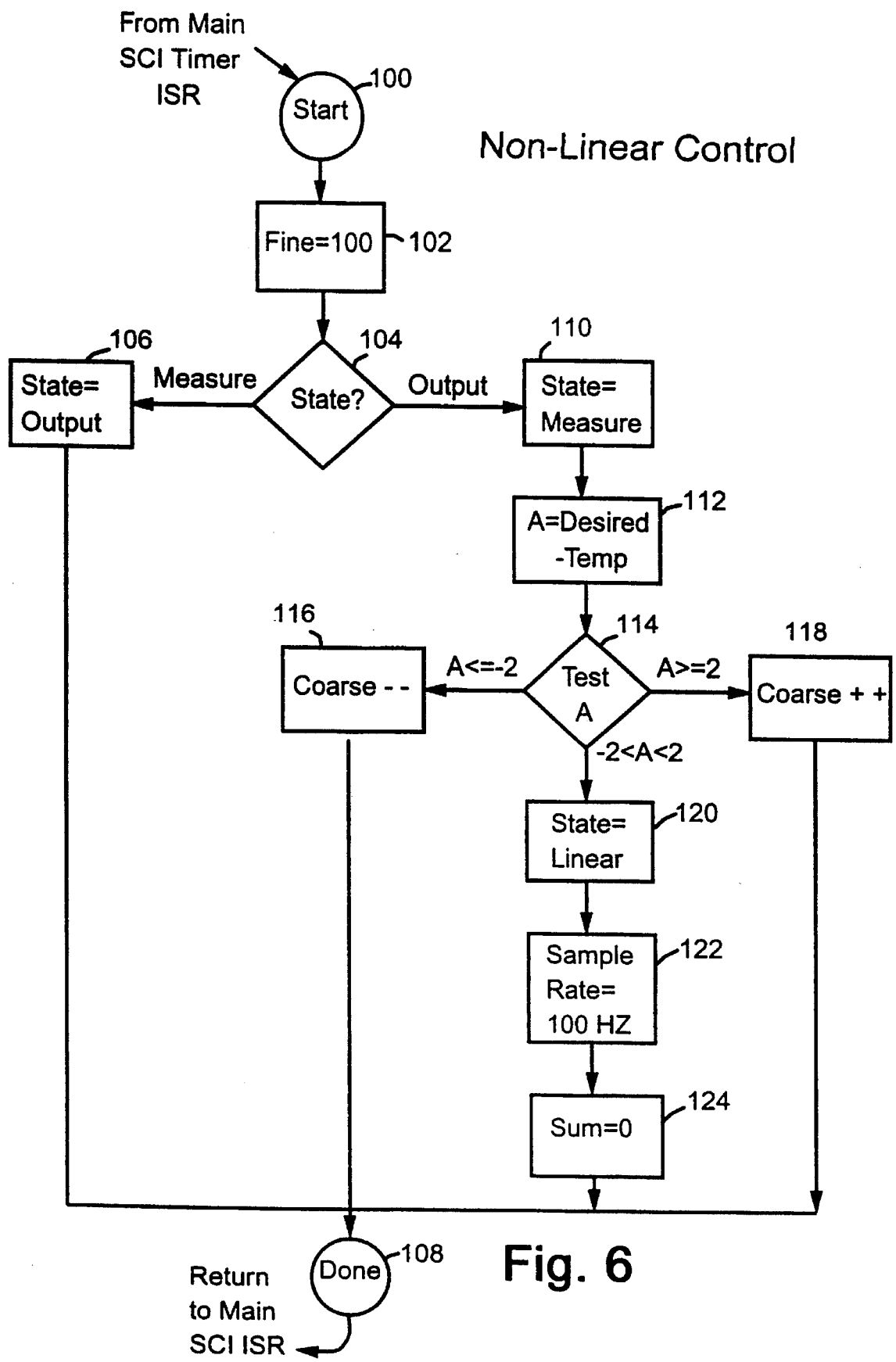
FIG. 6 is a high level flow diagram of a nonlinear control circuit constructed in accordance with the method and system of the present invention.

Referring now to FIG. 6, there is depicted a high level flow diagram of the nonlinear control circuit of the method and system of the present invention. As described above, the nonlinear control task is called from the two-state control system depicted in FIG. 4 and is executed at a rate of twenty times per second. The nonlinear control task always sets "FINE" to its midrange value of 100 as illustrated in block 102 and then adjusts the "COARSE" signal.

As depicted in FIG. 6, the nonlinear control system includes two sub-states which are referred to as "MEASURE" and "OUTPUT" which are determined at block 104. Initially, the system begins in the "MEASURE" state where the control system simply begins a frequency measurement by changing the state to "OUTPUT." After approximately 50 milliseconds, the nonlinear control task is called again and the frequency measurement is complete. During this period of time the nonlinear control state is in the "OUTPUT" state and the variable "TEMP" contains the number of timing track pulses which have occurred during the last 50 milliseconds. For speeds of 100, 200 and 400 millimeters per second, the variable "TEMP" should preferably be 160, 320, and 640 respectively. In the "OUTPUT" state, the nonlinear control task changes its state back to "MEASURE" for the next execution and then subtracts the variable "TEMP" from the desired value of 160, 320, or 640, as depicted at block 112.

Next, the process passes to block 114. Block 114 illustrates a determination of whether or not the difference between the desired presentation speed and the variable "TEMP" is less than or equal to −2, greater than or equal to 2, or between −2 and 2. If this value is greater than or equal to 2, the process passes to block 118 which illustrates the incrementing of the variable "COARSE." The process then returns, as depicted at block 108. However, in the event the difference is less than −2, the process passes to block 116 which illustrates the decrementing of the variable "COARSE" and the process then passes to block 108 and returns. Finally, in the event this difference lies between −2 and +2, the process passes from block 114 to block 120 which changes the state of the control system to linear operation. The process then passes to block 122 which depicts the changing of the sample rate to the rate utilized in linear mode and the setting of the error signal "SUM" to 0. The process then returns, as depicted at block 108. The gain of the variable "COARSE" is preferably chosen such that the transport deck will always reach its steady state response to a single least significant bit step change of the value of the variable "COARSE" within 50 milliseconds, when the next measurement will begin. In this manner, the nonlinear control system of the present invention guarantees stability for any input disturbances, no matter how great.

Upon reference to the foregoing those skilled in the art will appreciate that the Applicants herein have provided a novel two-state control system whereby a standard off-the-shelf tape transport deck may be utilized to provide precise time based presentation of recorded medical data by utilizing a two-state control system which includes an integrater while operating in a linear mode such that a zero steady state error can be induced over time and wherein large amplitude variations of input control signal which may result in a nonlinear response may be accommodated.

While the invention has been particularly shown and described with reference to a preferred embodiment, it will be understood by those skilled in the art that various changes in form and detail may be made therein without departing from the spirit and scope of the invention.

We claim:

1. A system for precise time based presentation of recorded data, said system comprising;
    a presentation device for presenting recorded data at an actual presentation speed which varies in response to variations of a variable speed control signal wherein actual presentation speed varies linearly in response to variations of said variable speed control signal which do not exceed a selected maximum during a given period of time and nonlinearly in response to variations of said variable speed control signal which exceed said selected maximum during a given period of time;

a speed control detection circuit coupled to said presentation device for periodically determining a difference between a desired presentation speed and said actual presentation speed; and a speed control signal generation circuit coupled to said speed control detection circuit and said presentation device for generating and varying said variable speed control signal in response to said difference between said desired presentation speed and said actual presentation speed, said speed control signal generation circuit comprising:

a linear control system for periodically varying said variable speed control signal at not greater than a first rate in response to a difference between said desired presentation speed and said actual presentation speed which results in a variation of said variable speed control signal which does not exceed said selected maximum during a given period of time and for coupling said variable speed control signal to said presentation device; and a nonlinear control system for periodically varying said variable speed control signal at a constant rate in response to a difference between said desired presentation speed and said actual presentation speed which results in a variation of said variable speed control signal wherein said variation does exceed said selected maximum during a given period of time and for coupling said variable speed control signal to said presentation device wherein said presentation device continues to operate in a stable manner despite the occurrence of large variations in presentation speed.

2. The precise time based presentation of recorded data according to claim 1, wherein said linear control system further includes an integration element for inducing a zero steady state error between said desired presentation speed and said actual presentation speed over time.

3. The precise time based presentation of recorded data according to claim 1, wherein said recorded data includes a timing track signal and wherein said system further includes a timing track signal detection circuit for determining said actual presentation speed.

4. The precise time based presentation of recorded data according to claim 3, wherein said timing track signal comprises a thirty-two Hertz square wave timing signal.

5. A system for recording and presenting time based medical data, said system comprising:

a recorder device for recording time based medical data;

a presentation device for presenting recorded data at an actual presentation speed which varies in response to variations of a variable speed control signal wherein actual presentation speed varies linearly in response to variations of said variable speed control signal which do not exceed a selected maximum during a given period of time and nonlinearly in response to variations of said variable speed control signal which exceed said selected maximum during a given period of time;

a speed control detection circuit coupled to said presentation device for periodically determining a difference between a desired presentation speed and said actual presentation speed; and a speed control signal generation circuit coupled to said speed control detection circuit and said presentation device for generating and varying said variable speed control signal in response to said difference between said desired presentation speed and said actual presentation speed, said speed control signal generation circuit comprising:

a linear control circuit for periodically varying said variable speed control signal at a first rate in response to a difference between said desired presentation speed and said actual presentation speed which results in a variation of said variable speed control signal which does not exceed said selected maximum and for coupling said variable speed control signal to said presentation device; and a nonlinear control system for periodically varying said variable speed control signal at a constant rate in response to a difference between said desired presentation speed and said actual presentation speed which results in a variation of said variable speed control signal wherein said variation does exceed said selected maximum during a given period of time and for coupling said variable speed control signal to said presentation device wherein said presentation device continues to operate in a stable manner despite the occurrence of large variations in presentation speed.

6. The precise time based presentation of recorded data according to claim 5, wherein said linear control system further includes an integration element for inducing a zero steady state error between said desired presentation speed and said actual presentation speed over time.

7. The precise time based presentation of recorded data according to claim 5, wherein said time based recorded medical data includes a timing track signal and wherein said system further includes a timing track signal detection circuit for determining said actual presentation speed.

8. The precise time based presentation of recorded data according to claim 7, wherein said timing track signal comprises a thirty-two Hertz square wave timing signal.

9. The precise time based presentation of recorded data according to claim 5, wherein said recorder device comprises an ambulatory heart recorder.

10. The precise time based presentation of recorded data according to claim 9, wherein said ambulatory heart recorder includes a plurality of electrodes.

11. A method for precise time based presentation of recorded data utilizing a presentation device which presents recorded data at an actual presentation speed which varies in response to a variations of variable speed control signal wherein said actual presentation speed varies linearly in response to variations of said variable speed control signal which do not exceed a selected maximum during a given period of time and nonlinearly in response to variations of said variable speed control signal which exceed said selected maximum during a given period of time, said method comprising the steps of:

periodically determining a difference between a desired presentation speed and said actual presentation speed;

periodically generating and varying said variable speed control signal in response to a difference between said desired presentation speed and said actual presentation speed at not greater than a first rate in response to a difference between said desired presentation speed and said actual presentation speed which results in a variation of said variable speed control signal which does not exceed said selected maximum during a given period of time and at a constant rate in response to a difference between said desired presentation speed and said actual presentation speed which results in a variation of said variable speed control signal which does exceed said selected maximum during a given period of time wherein said presentation device continues to operate in a stable manner despite the occurrence of large variations in presentation speed; and coupling said variable speed control signal to said presentation device.

* * * * *